United States Patent [19]
Shimada et al.

[11] Patent Number: 5,406,374
[45] Date of Patent: Apr. 11, 1995

[54] METHOD FOR DETECTING BUBBLES AND INCLUSIONS PRESENT IN OPTICAL FIBER PREFORM AND APPARATUS FOR DETECTING SAME

[75] Inventors: Tadakatsu Shimada; Kazuo Koya, both of Gunma, Japan

[73] Assignee: Shin-Etsu Chemical Co., Ltd., Tokyo, Japan

[21] Appl. No.: 111,665

[22] Filed: Aug. 25, 1993

[30] Foreign Application Priority Data

Aug. 27, 1992 [JP] Japan .................. 4-228738

[51] Int. Cl.$^6$ ............................................. G01N 21/88
[52] U.S. Cl. .................. 356/73.1; 356/239; 356/426
[58] Field of Search .............. 356/73.1, 237, 239, 356/426

[56] References Cited
U.S. PATENT DOCUMENTS 4,162,125  7/1979  Schmidt .................. 356/239 X
4,571,077  2/1986  Skeldon .................. 356/239

FOREIGN PATENT DOCUMENTS 1-253639  10/1989  Japan .................. 356/237

Primary Examiner—Vincent P. McGraw
Attorney, Agent, or Firm—McAulay Fisher Nissen Goldberg & Kiel

[57] ABSTRACT

A method and an apparatus for accurately, thoroughly and automatically inspecting an optical fiber preform for the presence of bubbles and/or inclusions are herein provided. The inspection apparatus comprises light source 2 for making light rays incident upon the end face 1a of rod-like optical fiber preform 1 as a subject to be inspected, video camera 7 for photographing the side face of the optical fiber preform 1 and image-processing circuit 11 for discriminating and detecting bubbles and/or inclusions present in the preform 1 through processing of image signals outputted from the video camera 7 and inputted to the circuit 11.

19 Claims, 2 Drawing Sheets

METHOD FOR DETECTING BUBBLES AND INCLUSIONS PRESENT IN OPTICAL FIBER PREFORM AND APPARATUS FOR DETECTING SAME

BACKGROUND OF THE INVENTION

The present invention relates to a method for photoelectrically detecting the presence of bubbles and/or inclusions in an optical fiber preform as well as an apparatus for detecting these bubbles and/or inclusions.

Bubbles and inclusions present in an optical fiber become causes of fatal defects, since they scatter and/or absorb light rays which transmit through the optical fiber to thus attenuate the intensity of the transmitting light rays and reduce the strength of the optical fiber. When drawing an optical fiber preform into an optical fiber, the optical fiber may sometimes be broken due to the presence of these bubbles and inclusions. It is thus needed to inspect an optical fiber preform for the presence of bubbles and inclusions prior to drawing it into an optical fiber in order to eliminate the foregoing problems. An optical fiber preform has conventionally been inspected for the presence of bubbles and/or inclusions by making light rays incident upon the preform and visually observing the preform, with the naked eyes, for the presence of bright spots formed by the bubbles and/or inclusions present therein which scatter the light rays incident upon the preform. This is one of sensory tests and therefore, there are differences between individuals in the detection of such bright spots. Moreover, there has been desired for the establishment of a method for mechanically inspecting optical fiber preforms, for the elimination of the foregoing problem and for the elimination or reduction of labor.

A method for inspecting the influence of bubbles present in a quartz tube used as a jacket for an optical fiber on various properties of the resulting optical fiber was reported at the Annual Meeting, the 59th year of Showa, of Electronics Telecommunication Society of Japan, A National Convention of the Branch of Optics Radio Wave. The gist thereof is disclosed in the article entitled "Effects of Bubbles Present in Quartz Tubes on the Strength of Optical Fibers", the published Resume for the Meeting, 2-165, 421. According to this article, the method comprises making a laser beam incident upon the end face of a quartz tube while rotating the quartz tube and detecting light rays scattered and reflected by bubbles present in the tube with a photomultiplier. The quartz tube is irradiated with the laser beam along the circumference of the tube as the tube is rotated and the quartz tube can be inspected by scanning the photomultiplier along the longitudinal direction of the tube.

However, this method is inconvenient for the detection of bubbles throughout the whole length of the quartz tube. This is because, the cross sectional area of the laser beam is substantially smaller than the thickness of the quartz tube and accordingly, it is impossible to irradiate the whole cross section of the tube with the laser beam. When inspecting, in particular, a subject having a circular cross section such as an optical fiber preform, only a part thereof can be inspected by irradiating the cross section thereof with a laser beam. For this reason, there has not yet been proposed any method for mechanically detecting bubbles and/or inclusions present in an optical fiber preform.

SUMMARY OF THE INVENTION

The present invention has been developed for the purpose of solving the foregoing problems associated with the conventional techniques for inspecting an optical fiber preform for the presence of bubbles and/or inclusions and accordingly, an object of the present invention is to provide a method for automatically and accurately inspecting an optical fiber preform throughout the entire cross section and length thereof for the presence of bubbles and/or inclusions as well as an apparatus for practicing the method.

The method for inspecting an optical fiber preform for the presence of bubbles and/or inclusions according to the present invention comprises making light rays incident upon the whole end face of a rod-like optical fiber preform, photographing an image of the side face of the optical fiber preform by a video camera and analyzing the image signals of the photographed image to detect and discriminate bubbles and/or inclusions.

According to another aspect of the present invention, the method for inspecting an optical fiber preform for the presence of bubbles and/or inclusions comprises making light rays incident upon the whole end face of a rod-like optical fiber preform, photographing an image of the side face of the optical fiber preform by a video camera, differentiating the image signals of the photographed image with respect to intensity change in the direction of the longitudinal axis of the optical fiber preform and comparing the resulting differential value with a predetermined reference value to thus detect and discriminate bubbles and/or inclusions which are defined to be bright spots whose value obtained through the differentiation is not less than the reference value.

The inspection of the rod-like optical fiber preform may be performed in the air or the preform may be inspected while dipping it in a matching oil.

When a rod-like optical fiber preform is inspected, in particular, in the air, the detection and discrimination of the presence of bubbles and/or inclusions are preferably carried out by differentiating the image signals of the photographed image with respect to intensity change in the direction of the longitudinal axis of the optical fiber preform and comparing the resulting differential value with the predetermined reference value to thus determine whether the former is greater than the latter and to detect and discriminate bubbles and/or inclusions which are defined to be bright spots whose value obtained through the differentiation is not less than the reference value.

In the foregoing inspection method, it is preferred to make light rays incident upon the optical fiber preform and photograph the images of the preform by the video camera while rotating the optical fiber preform around the longitudinal axis of the optical fiber preform.

According to a further aspect of the present invention, there is provided an apparatus for inspecting an optical fiber preform for the presence of bubbles and/or inclusions which comprises, as will be seen from FIG. 1 showing an embodiment of the present invention, light source 2 for making light rays incident upon end face 1a of rod-like optical fiber preform 1 as a subject to be inspected, video camera 7 for taking photographs of images of the side face of the preform 1 and image-processing (or -analyzing) circuit 11 for detecting and discriminating bubbles and/or inclusions on the basis of image signals outputted from the video camera 7 and inputted thereto.

The image-processing circuit 11 comprises, as shown in FIG. 2, differentiation circuit 15 which differentiates the image signals with respect to the intensity change along the direction of the longitudinal axis of the optical fiber preform and discrimination circuit 17 for comparing the value obtained through the differentiation performed by the differentiation circuit 15 with a reference value and this structure permits the elimination of any influence, on the inspection, of the light rays scattered by the outer surface of the optical fiber preform 1.

As will be seen from FIG. 3, any influence of the light rays scattered by the outer surface of the optical fiber preform 1 may likewise be eliminated if the apparatus is designed such that it is provided with means 25 for dipping the optical fiber preform 1 as the subject to be inspected in a matching oil.

The inspection apparatus preferably comprises driving means 20 for rotating the optical fiber preform 1 around the longitudinal axis of the preform 1 as shown in FIG. 1.

In the inspection apparatus shown in FIG. 1, the whole end face 1a of the rod-like optical fiber preform 1 is irradiated with light rays emitted from the light source 2. The incident light rays are scattered by bubbles and/or inclusions present in the preform 1. At this stage, the side face of the preform 1 is photographed by the video camera 7 and the images of these bubbles and/or inclusions are simultaneously photographed by the video camera 7. The image signals are outputted from the video camera 7 and then inputted to the image-processing circuit 11 which processes the image signals to detect and discriminate bubbles and/or inclusions present in the preform. If bubbles and/or inclusions are not present in the optical fiber preform 1, the light rays incident upon the end 1a transmit through the optical fiber preform without causing any scattering and any image is not detected by the video camera 7. Thus, it can be concluded that the optical fiber preform 1 is substantially free of bubbles and/or inclusions.

When the rod-like optical fiber preform 1 is examined in the air as shown in FIG. 1, reflected images formed by the outer surface of the preform 1 serve as noises during photographing the preform 1 by the video camera 7 and often make the discrimination or detection of bubbles and/or inclusions difficult. However, these bubbles and/or inclusions can correctly be discriminated if the image-processing circuit 11 has a structure as shown in FIG. 2. More specifically, image signals relating to bubbles and/or inclusions present in the optical fiber preform 1 exhibit rapid change in the intensity along the longitudinal axis of the preform 1, while image signals corresponding to the images formed due to the reflection of light by the outer surface of the preform 1 do not show any significant change in the intensity along the longitudinal axis of the preform 1. Therefore, the image signals outputted from the video camera 7 are differentiated with respect to the intensity change in the direction of the longitudinal axis of the preform 1 through the action of the differentiation circuit 15 and the value obtained through the differentiation operation performed in the differentiation circuit 15 is compared with a reference value previously stored in discrimination circuit 17 to detect and discriminate bubbles and/or inclusions which are defined to be positions whose value obtained through the differentiation is not less than the reference value and to thus eliminate any influence of the light rays scattered by the outer surface of the optical fiber preform 1.

When a rod-like optical fiber preform 1 is inspected for the presence of bubbles and/or inclusions while dipping the preform in a matching oil, bright spots formed on the photographs taken by the video camera 7 are ascribed to bubbles and/or inclusions present in the preform 1, since the outer surface of the preform does not affect these bright spots.

As has been shown in FIG. 3, any influence of the reflection by the outer surface of the optical fiber preform 1 on the detection or discrimination of bubbles and/or inclusions can be eliminated by making use of means 25 for dipping the preform 1 in a matching oil during the inspection and, therefore, any image formed through the reflection of light rays on the outer surface of the preform 1 is not detected by the video camera 7. Thus, bright spots formed on the photographs taken by the video camera 7 are correctly ascribed to bubbles and/or inclusions present in the preform 1.

As has been explained above in detail, the method and apparatus of the present invention permit correct, thorough and automatic detection of bubbles and/or inclusions present in an optical fiber preform 1. Moreover, the method and apparatus permit the elimination of the need for macroscopic inspection in which bubbles and/or inclusions are observed with the naked eyes which has conventionally been adopted and serve to economize the inspection of the optical fiber preforms. Thus, the method and apparatus according to the present invention allows the elimination of various drawbacks associated with the production of optical fibers, at the stage of the preform. For instance, they can prevent any breakage of an optical fiber during drawing an optical fiber preform into an optical fiber and can prevent the formation of optical fibers having poor transmittance.

DETAILED EXPLANATION OF THE INVENTION

Embodiments of the method and apparatus of the present invention will hereinafter be described in more detail.

Figure 1:
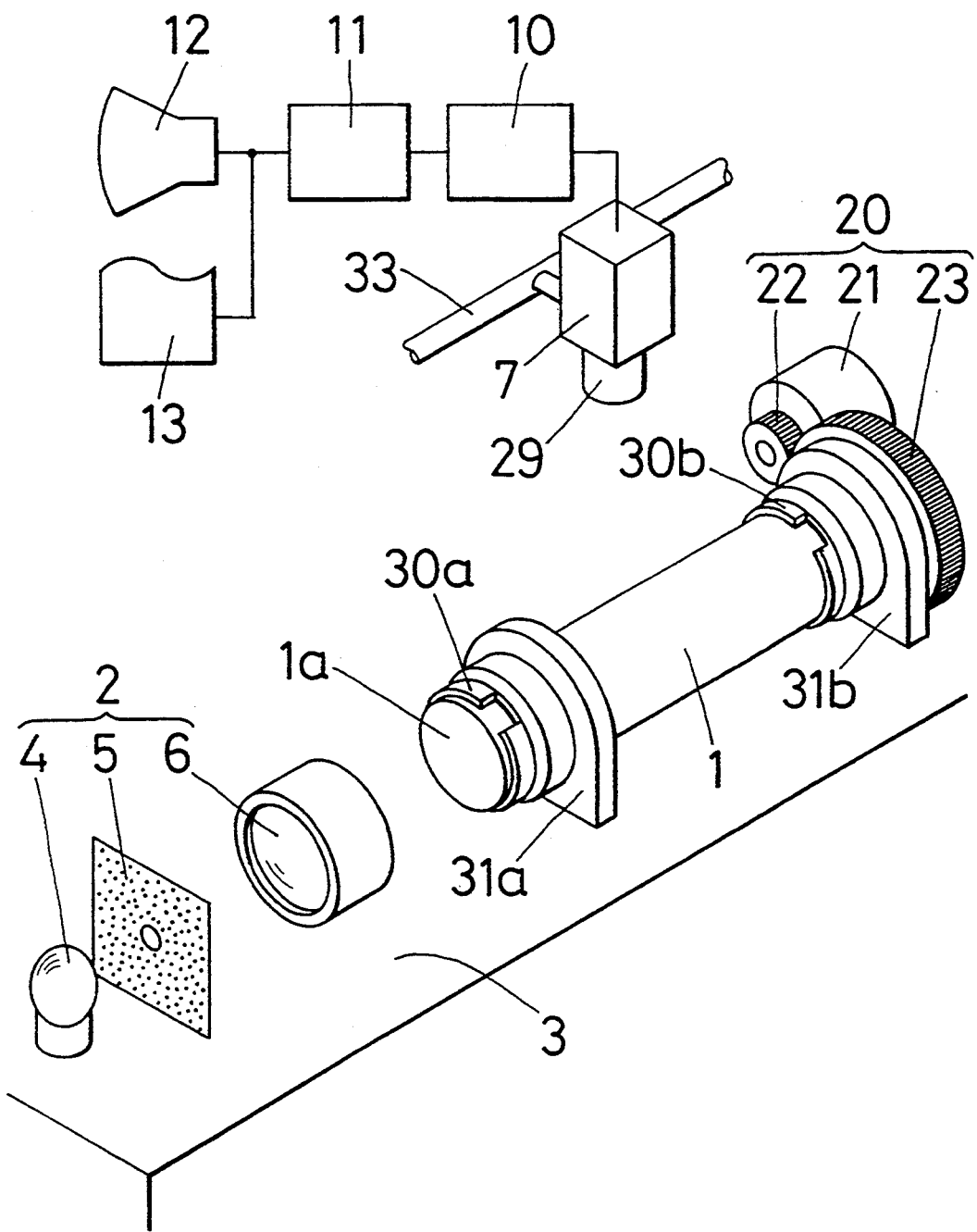
FIG. 1 is a perspective view showing an embodiment of the apparatus for inspecting an optical fiber preform for the presence of bubbles and/or inclusions according to the present invention.

FIG. 1 is a perspective view showing an embodiment of the apparatus for inspecting an optical fiber preform for the presence of bubbles and/or inclusions according to the present invention. The inspection apparatus shown in FIG. 1 is assembled on chassis 3 and comprises light source 2 emitting light rays which are incident upon the whole end face 1a of optical fiber preform 1, video camera 7 for taking a photograph of the side face of the optical fiber preform 1 and image-processing circuit 11 for detecting and discriminating bubbles and/or inclusions present in the preform 1 through processing of the image signals outputted from the video camera 7 and inputted to the circuit 11. The optical fiber preform 1 is connected to rotating-driving means 20 which comprises motor 21 and gears 22 and 23.

One end of the optical fiber preform 1 is held in chuck 30a fitted to rotary holder 31a and the end 1a thereof is exposed and positioned on the side of the light source 2. Another end of the preform 1 is held in chuck 30b fitted to rotary holder 31b. The gear 23 is fitted to a rotary shaft of the chuck 30b and engages with the gear 22 connected to the motor 21.

The light source 2 comprises white lamp 4, aperture mask 5 and condenser lense 6, wherein the aperture mask 5 is positioned at the focal point of the condenser lense 6. The aperture of the condenser lense 6 has a size sufficient for allowing the encompassment of the whole end face 1a of the optical fiber preform 1 and the light rays emitted from the white lamp 4 is uniformly incident upon the whole end face 1a of the optical fiber preform 1 in the form of approximately parallel rays.

The video camera 7 is a CCD (charge coupled device) camera and photographing lense 29 is slidably fitted to frame 33, fixed to the chassis 3, in such a manner that the lense 29 faces the side face of the optical fiber preform 1 and is parallel to the longitudinal direction of the preform 1. The photographing range which is encompassed by the photographing lense 29 corresponds to the range of the optical fiber preform 1 capable of being inspected. If the photographing range does not embrace the whole longitudinal length of the optical fiber preform 1, the optical fiber preform 1 can be separately inspected, over several times, throughout the whole longitudinal length thereof by sliding the video camera 7 along the frame 33. In general, the thickness of the optical fiber preform 1 is substantially smaller than the length thereof and, therefore, the inspection of the whole range in the direction of the thickness of the preform can be ensured by a single photographing.

The video camera 7 is connected to memory 10 for storing the photographed image signals, to image-processing circuit 11 for detecting and discriminating bubbles and/or inclusions through the processing of the image signals invoked from the memory 10, to display device 12 for displaying the bubbles and/or inclusions detected by the image-processing circuit 11 and to printer 13 for printing out the contents displayed on the device 12.

Figure 2:
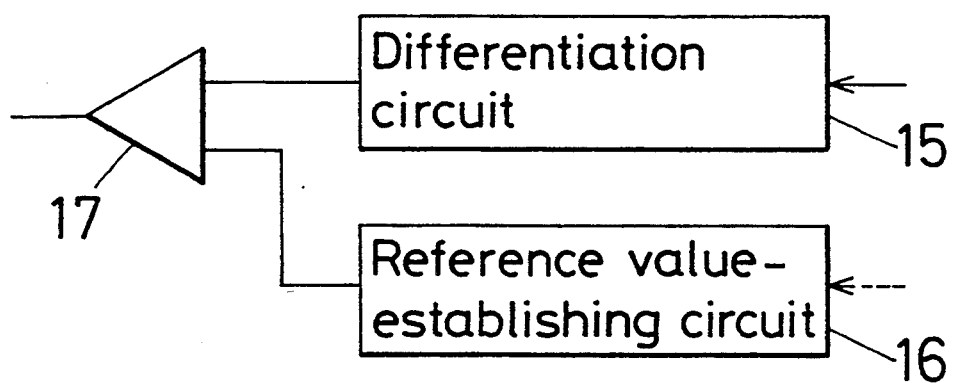
FIG. 2 is a block diagram showing an embodiment of an image-processing circuit used in the inspection apparatus according to the present invention.

As will be seen from FIG. 2, the image-processing circuit 11 comprises differentiation circuit 15, reference value-establishing circuit 16 and comparison-discrimination circuit 17. The differentiation circuit 15 performs differentiation of image signals with respect to the intensity change thereof in the direction of the longitudinal axis of the preform 1 to thus determine the rate of variation (magnification of the change in the intensity of the image signals). The reference value-establishing circuit 16 can establish a reference value which is n times the rate of variation (wherein n ranges from 2 to 20). The comparison-discrimination circuit 17 compares the rate of variation determined by the differentiation circuit 15 with the reference rate of variation (threshold level) established by the reference value-establishing circuit 16, then judges whether the value obtained through the differentiation is greater than the threshold level or not to thus discriminate bubbles and/or inclusions present in the optical fiber preform 1 whose value obtained through the differentiation is not less than the threshold level and outputs the coordinates of these bubbles and/or inclusions to the display device 12 and the printer 13.

A sample of an optical fiber preform which has been proved to have 6 bubbles having a diameter on the order of about 0.1 mm was practically inspected by fitting it to the inspection apparatus having the structure as shown in FIG. 1. The reference rate of variation in the reference value-establishing circuit 16 of the image-processing circuit 11 was set to 5 times (i.e., n=5). When the white lamp 4 is lighted, light rays emitted from the lamp were uniformly incident upon the end face 1a of the optical fiber preform 1. The light rays were scattered by bubbles present in the optical fiber preform 1, the resulting optical image was photographed by the video camera 7, the image signal outputted from the video camera was processed in the image-processing circuit 11 and displayed on the display device 12. At this stage, these 6 fine bubbles having a diameter on the order of about 0.1 mm were all displayed on the device 12 and simultaneously spots were appeared at the positions corresponding to the line showing the external shape of the optical fiber preform 1. However, these spots displayed at the positions corresponding to the line showing the external shape of the preform 1 were disappeared and only these 6 bubbles were displayed on the device 12 when the reference rate of variation in the reference value-establishing circuit 16 was reset to 10 times (i.e., n=10). Thus, only the coordinates of these bubbles could be confirmed.

By way of comparison, the following inspection was performed. An apparatus used in this inspection was slightly different, from that shown in FIG. 1, in the structure of the image-processing circuit 11. More specifically, the comparison-discrimination circuit 17 of this image-processing circuit 11 compares the intensity of an image signal with the established reference value of n times the intensity of the signal serving as the threshold level. The established reference value was set to 20 times (i.e., n=20) and the same sample of an optical fiber preform used in the foregoing example was inspected. Strong noises were appeared on the display device 12 at the positions corresponding to the line showing the external shape of the preform 1 and accordingly, any clear images of the fine bubbles could not be displayed on the device 12. At this stage, when the reference rate of variation in the reference value-establishing circuit 16 was gradually increased and reset to 50 times (i.e., n=50), the noises were attenuated to an extent that spots were displayed on the device 12 at the positions corresponding to the line showing the external shape of the preform 1, but 2 bubbles having smaller diameters out of these 6 bubbles were disappeared (only 4 bubbles were displayed and thus confirmed). Moreover, when the reference rate of variation was reset to 80 times (i.e., n=80), the noises corresponding to the line showing the external shape of the preform 1 were completely disappeared, but 1 additional fine bubble having a smaller diameter was also disappeared and only 3 out of the 6 bubbles could be confirmed.

When the motor 21 of the apparatus shown in FIG. 1 is operated, the rotational motion thereof is transmitted to the gears 22 and 23 and as a result, the optical fiber preform 1 is rotated. If the motor 21 is not operated, only the coordinates of bubbles and/or inclusions present along the longitudinal direction of the preform 1 can be confirmed since the positions of these bubbles and/or inclusions displayed on the display device 12 are not changed. On the other hand, when the motor 21 is operated, the positions of bubbles and/or inclusions displayed on the device 12 cause fluctuation due to the rotational motion of the preform 1 and accordingly, the precise positions of these bubbles and/or inclusions in a particular cross sectional area of the preform 1 can be confirmed.

Figure 3:
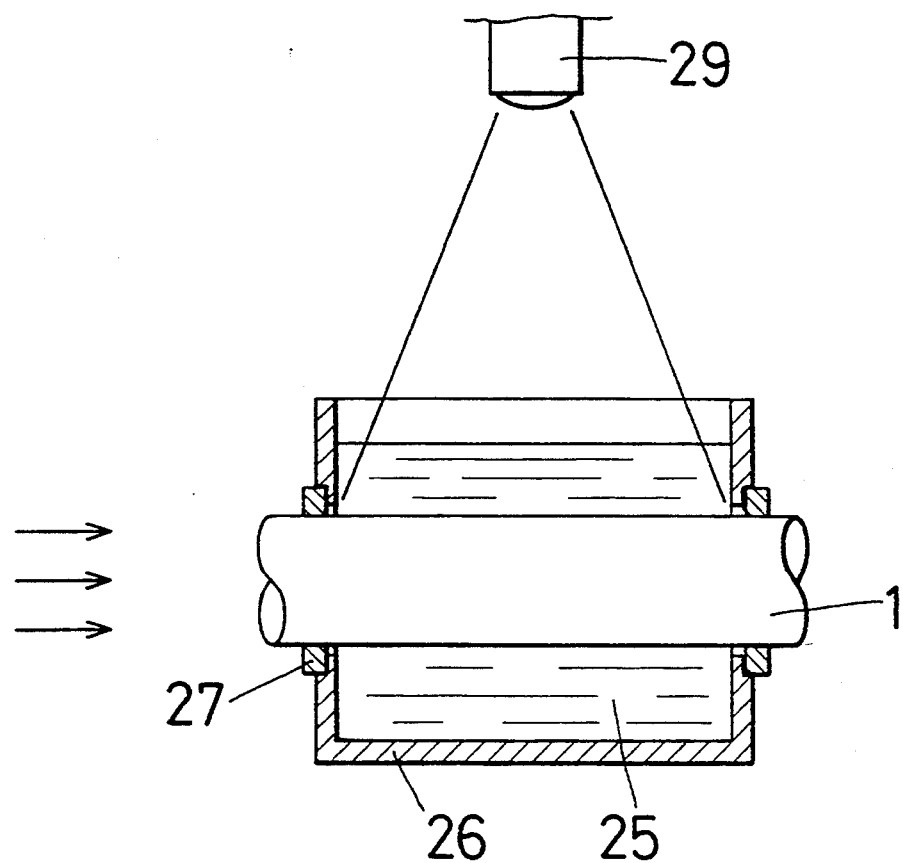
FIG. 3 is a cross sectional view of an embodiment of the apparatus of the present invention, which permits removal of noises generated due to the line showing the external shape of the optical fiber preform.

FIG. 3 shows another embodiment of the apparatus according to the present invention, which is capable of removing noises generated due to the line showing the external shape of the optical fiber preform 1. This apparatus shown in FIG. 3 has a structure identical to that shown in FIG. 1 except that the optical fiber preform 1 is dipped in matching oil 25. In FIG. 3, the reference numeral 26 represents a container of the matching oil 25 and the reference numeral 27 represents a packing. The matching oil 25 is an oil having a refractive index approximately identical to that of the optical fiber preform 1. Light rays are incident upon the end face of the preform 1 from the direction indicated by an arrow and the side face of the preform 1 is photographed by the video camera 7 (not shown in FIG. 3) through the photographing lense 29 and the matching oil 25. The line showing the external shape of the preform 1 is not detected by the video camera 7 due to the presence of the matching oil and the video camera 7 simply receives images of bright spots formed through scattering of the light rays by bubbles and/or inclusions present in the optical fiber preform 1. For this reason, the use of the foregoing image-processing circuit 11 is not necessary in this embodiment.

In the foregoing embodiments, white lamp 4 is used as a light source, but the use of a source of diffused light such as a halogen lamp and a tungsten lamp is effective since light rays emitted from the source can be incident upon the whole end face 1a of the optical fiber preform 1.

What is claimed is:

1. A method for inspecting a rod-like optical fiber preform for the presence of bubbles and/or inclusions thereof comprising the steps of photographing images scattered by the bubbles and/or inclusions through a side face of the preform by a video camera while light rays are incident upon the whole end face of the preform from a white lamp and discriminating and detecting the bubbles and/or inclusions through image-analysis of image signals of the photographed images.

2. The method for inspecting an optical fiber preform for the presence of bubbles and/or inclusions according to claim 1 wherein the photographing of the rod-like optical fiber preform is carried out while dipping the optical fiber preform in a matching oil.

3. The method for inspecting an optical fiber preform for the presence of bubbles and/or inclusions according to claim 1 wherein the step of photographing the optical fiber preform with the light rays incident thereon is carried out while rotating the optical fiber preform around the longitudinal axis as a center.

4. The method for inspecting an optical fiber preform for the presence of bubbles and/or inclusions according to claim 2 wherein the step of photographing the optical fiber preform with the light rays incident thereon is carried out while rotating the optical fiber preform around the longitudinal axis as a center.

5. A method for inspecting a rod-like optical fiber preform for the presence of bubbles and/or inclusions comprising the steps of photographing images scattered by the bubbles and/or inclusions through a side face of the preform while light rays from a white lamp are incident upon the whole end face of the preform, differentiating image signals of the photographed images with respect to intensity change thereof along the direction of the longitudinal axis of the preform and comparing the differential value with a pre-established reference value to discriminate and detect the bubbles and/or inclusions which are defined to be bright spots whose value obtained through the differentiation is not less than the reference value.

6. The method for inspecting an optical fiber preform for the presence of bubbles and/or inclusions according to claim 5 wherein the photographing of the rod-like optical fiber preform is carried out while dipping the optical fiber preform in a matching oil.

7. The method for inspecting an optical fiber preform for the presence of bubbles and/or inclusions according to claim 5 wherein the photographing of the rod-like optical fiber preform is carried out while the optical fiber preform is placed in the air.

8. The method for inspecting an optical fiber preform for the presence of bubbles and/or inclusions according to claim 5 wherein the step of photographing the optical fiber preform with the light rays incident thereon is carried out while rotating the optical fiber preform around the longitudinal axis as a center.

9. The method for inspecting an optical fiber preform for the presence of bubbles and/or inclusions according to claim 6 wherein the step of photographing the optical fiber preform with the light rays incident thereon is carried out while rotating the optical fiber preform around the longitudinal axis as a center.

10. The method for inspecting an optical fiber preform for the presence of bubbles and/or inclusions according to claim 7 wherein the step of photographing the optical fiber preform with the light rays incident thereon is carried out while rotating the optical fiber preform around the longitudinal axis as a center.

11. An apparatus for inspecting a rod-like optical fiber preform for the presence of bubbles and/or inclusions comprising a white light source adapted for making light rays incident upon the whole end face of the preform, a video camera for photographing images reflected by the bubbles and/or inclusions through a side face of the preform and an image-processing circuit for discriminating and detecting the bubbles and/or inclusions in the preform through processing of image signals outputed from the video camera.

12. The apparatus for inspecting an optical fiber preform for the presence of bubbles and/or inclusions according to claim 11 wherein the image-processing circuit comprises a differentiation circuit for differentiating the image signals with respect to intensity change along the direction of the longitudinal axis of the optical fiber preform and a discrimination circuit for comparing the differential value obtained through the differentiation by the differentiation circuit with a reference value.

13. The apparatus for inspecting an optical fiber preform for the presence of bubbles and/or inclusions according to claim 11 further comprising means for dipping the subject to be inspected in a matching oil.

14. The apparatus for inspecting an optical fiber preform for the presence of bubbles and/or inclusions according to claim 12 wherein it is further provided with a means for dipping the subject to be inspected in a matching oil.

15. The apparatus for inspecting an optical fiber preform for the presence of bubbles and/or inclusions according to claim 11 further comprising driving means for rotating the optical fiber preform around the longitudinal axis as a center.

16. The apparatus for inspecting an optical fiber preform for the presence of bubbles and/or inclusions according to claim 12 further comprising driving means for rotating the optical fiber preform around the longitudinal axis as a center.

17. The apparatus for inspecting an optical fiber preform for the presence of bubbles and/or inclusions according to claim 13 further comprising driving means for rotating the optical fiber preform around the longitudinal axis as a center.

18. The apparatus for inspecting an optical fiber preform for the presence of bubbles and/or inclusions according to claim 14 further comprising driving means for rotating the optical fiber preform around the longitudinal axis as a center.

19. A method for inspecting an optical fiber preform having a longitudinal axis, a side face substantially parallel to the longitudinal axis, and an end face substantially perpendicular to the longitudinal axis and covering a predetermined area, the method comprising the steps of:
   supplying light energy to the end face, the light energy being applied to the end face and covering the predetermined area;
   photographing the side face of the preform to obtain image signals; and
   performing image analysis on the image signals to detect imperfections in the optical fiber preform.

* * * * *